US009050192B2

(12) United States Patent
Mansmann

(10) Patent No.: US 9,050,192 B2
(45) Date of Patent: Jun. 9, 2015

(54) CARTILAGE REPAIR IMPLANT WITH SOFT BEARING SURFACE AND FLEXIBLE ANCHORING DEVICE

(75) Inventor: Kevin A. Mansmann, Paoli, PA (US)

(73) Assignee: Formae, Inc., Paoli, PA (US)

( * ) Notice: Subject to any disclaimer, the term of this patent is extended or adjusted under 35 U.S.C. 154(b) by 1430 days.

(21) Appl. No.: 10/071,930

(22) Filed: Feb. 8, 2002

(65) Prior Publication Data

US 2002/0173855 A1 Nov. 21, 2002

Related U.S. Application Data

(60) Provisional application No. 60/265,921, filed on Feb. 5, 2001.

(51) Int. Cl.
*A61F 2/30* (2006.01)
*A61L 27/52* (2006.01)
*A61F 2/32* (2006.01)
(Continued)

(52) U.S. Cl.
CPC ......... *A61F 2/30756* (2013.01); *A61F 2/30965* (2013.01); *A61F 2/32* (2013.01); *A61F 2/38* (2013.01); *A61F 2/40* (2013.01); *A61F 2/4618* (2013.01); *A61F 2002/30006* (2013.01); *A61F 2002/30011* (2013.01); *A61F 2002/30016* (2013.01); *A61F 2002/30065* (2013.01); *A61F 2002/30143* (2013.01); *A61F 2002/30148* (2013.01); *A61F 2002/30153* (2013.01); *A61F 2002/302* (2013.01); *A61F 2002/30225* (2013.01); *A61F 2002/30448* (2013.01); *A61F 2002/30451* (2013.01); *A61F 2002/30604* (2013.01); *A61F 2002/30751* (2013.01); *A61F 2002/30787* (2013.01); *A61F 2002/30789* (2013.01); *A61F 2002/30841* (2013.01); *A61F 2002/30892* (2013.01); *A61F 2002/30894* (2013.01); *A61F 2002/30957* (2013.01); *A61F 2002/30971* (2013.01); *A61F 2002/30973* (2013.01); *A61F 2002/4631* (2013.01); *A61F 2002/4635* (2013.01); *A61F 2210/0071* (2013.01); *A61F 2220/005* (2013.01); *A61F 2220/0058* (2013.01); *A61F 2230/0017* (2013.01); *A61F 2230/0019* (2013.01); *A61F 2230/0065* (2013.01);
(Continued)

(58) Field of Classification Search
CPC ... A61F 2/844; A61F 2/30; A61F 2002/4635; A61F 2002/5086; A61F 2/30756; A61F 2/3603; A61L 27/52
USPC .......... 623/23.72, 13.11, 13.12, 14.12, 18.11, 623/20.14, 20.28, 20.32, 20.33, 22.13, 623/22.14, 23.42, 23.57–23.61, 623/19.11–19.14, 21.12, 21.13, 21.15, 623/21.16, 21.18, 21.19
See application file for complete search history.

(56) References Cited

U.S. PATENT DOCUMENTS 4,502,161 A * 3/1985 Wall ........................... 623/14.12
4,769,040 A * 9/1988 Wevers ..................... 623/20.32
(Continued)

*Primary Examiner* — Christopher D Prone
(74) *Attorney, Agent, or Firm* — Duane Morris LLP

(57) ABSTRACT

A surgical implant for replacing hyaline cartilage in a knee or other articulating synovial joint has an anchoring side on one side of the implant adapted for fixing the implant to one of the bones in the joint, and a bearing surface on the opposite side of the implant for lubricious rubbing and sliding contact with another bone in the joint. The anchoring side can be configured with an irregular surface for tissue ingrowth. The bearing side can include hydrogel. The implant can be rolled up from an original shape and surgically inserted by arthroscopic means, and opens into its original shape when released inside the joint.

7 Claims, 4 Drawing Sheets

(51) Int. Cl.
*A61F 2/38* (2006.01)
*A61F 2/40* (2006.01)
*A61F 2/46* (2006.01)

(52) U.S. Cl.
CPC .............. *A61F 2230/0069* (2013.01); *A61F 2250/0015* (2013.01); *A61F 2250/0018* (2013.01); *A61F 2250/0019* (2013.01); *A61F 2250/0023* (2013.01); *A61F 2310/00293* (2013.01); *A61F 2310/00365* (2013.01); *A61L 27/52* (2013.01)

(56) References Cited

U.S. PATENT DOCUMENTS

| | | | | |
|---|---|---|---|---|
| 5,314,478 | A * | 5/1994 | Oka et al. | 623/14.12 |
| 5,368,602 | A * | 11/1994 | de la Torre | 606/151 |
| 5,735,903 | A * | 4/1998 | Li et al. | 128/898 |
| 6,132,468 | A * | 10/2000 | Mansmann | 623/20.16 |
| 6,764,514 | B1 * | 7/2004 | Li et al. | 623/17.12 |
| 2001/0039455 | A1 | 11/2001 | Simon | |

* cited by examiner

CARTILAGE REPAIR IMPLANT WITH SOFT BEARING SURFACE AND FLEXIBLE ANCHORING DEVICE

RELATED APPLICATION

This application claims the benefit, under 35 USC 119(e), of provisional patent application No. 60/265,921, filed on Feb. 5, 2001.

FIELD OF THE INVENTION

This invention is in the field of surgery, and more particularly relates to surgical implants for replacing damaged cartilage in joints such as knees, hips, and shoulders.

BACKGROUND OF THE INVENTION

Numerous efforts have been made to create various types of surgical methods and implants that can repair or replace damaged or diseased cartilage segments, in mammalian joints such as knees, hips, and shoulders. Those efforts generally can be divided into two categories: (1) non-resorbable implants, designed to remain in a repaired joint for the entire remaining life of the patient; and (2) resorbable implants, made of materials that will gradually dissolve and be replaced by natural biological materials.

It also should be noted that most types of resorbable implants are designed for regeneration of cartilage by living cells, rather than for replacing cartilage by synthetic polymers or other non-living materials. Cartilage regeneration efforts using resorbable implants usually involve transplantation of chondrocyte and/or mesenchymal cells, and the resorbable implants are designed to shelter and nurture the transplanted cells, allowing them to be "seeded" into the resorbable implant a week or so prior to implantation, thereby giving the cells a "headstart" before they are transplanted into the damaged joint.

At the current time, the devices discussed herein fall into the category of non-resorbable implants, made of synthetic materials and designed to remain in a joint for the remaining life of the patient. These implants will be used to replace, rather than regenerate, a cartilage segment that has become damaged or diseased. Accordingly, this current invention, as described and claimed below, is limited to non-resorbable implants, designed for replacement rather than regeneration of damaged cartilage.

Nevertheless, it should be recognized that, as research on these devices progresses, it may also be possible to adapt these devices for use in: (i) implants that use resorbable materials; and/or, (ii) cell-transplanting operations, designed to promote the regeneration of cartilage by transplanted cells. Accordingly, this current invention is not intended to close off and deny those possibilities; instead, this invention is intended as a focused and targeted step forward in the development of a highly useful class of non-resorbable implants, with the understanding that this technical development might also be extendible, in the future, to a different and distinct approach to cartilage repair.

In a similar manner, at the current time, any references herein to "implant", "device", or similar terms are limited to devices that will be implanted surgically, into a mammalian joint, to repair or replace a segment of hyaline cartilage. As known to those skilled in the art, hyaline cartilage is the term used to describe the type of cartilage that covers the condyles (rounded ends) of articulating bone surfaces, in joints such as knees, hips, shoulders, fingers, wrists, etc.

Two other types of cartilage (known as elastic cartilage, and fibrocartilage) also exist in mammals, and are present in the ears, nose, windpipe, etc. If desired, the invention disclosed herein can be adapted for use in repairing elastic cartilage and/or fibrocartilage. However, it should be recognized that, because of the compressive and shear forces involved, replacing damaged hyaline cartilage in load-bearing joints (especially the knees, hips, and shoulders) is much more difficult than replacing cartilage in the ears, nose, or other locations in the body. Accordingly, the only prior art which is regarded as relevant herein involves efforts to repair damaged hyaline cartilage knees, hips, shoulders, or ankles. Any other type of cartilage repair (including repair of damaged cartilage in finger joints) will not have to meet or satisfy the types of mechanical stresses that will be placed on cartilage segments in joints such as the knees, hips, or shoulders.

A major goal of this invention is to provide non-resorbable devices that can be inserted into a damaged or diseased joint using "minimally invasive" methods and tools, which includes arthroscopic methods and tools. However, it should be recognized that some of the devices disclosed herein may be able to provide improved implants that can be implanted using older "classical" or "open joint" surgical methods. In addition, it should be recognized that there is not always a clear dividing line between classical surgical methods (often referred to as "open joint" methods) and "minimally invasive" methods, since any competent surgeon will always minimize the amount of cutting and other damage and disruption to muscles, ligaments, blood vessels, and other tissues, in any surgical operation, in view of the needs of the operation and the patient.

Accordingly, any use herein of broad terms such as "surgery" or "surgical" are deemed to include arthroscopic and other minimally invasive methods; and, whenever use is made of a narrow term such as "arthroscopic", it should be realized that arthroscopic use is the primary goal of this invention, but the devices disclosed herein may also be adapted for use with other (classical, open joint) surgical methods.

Background information on non-resorbable implants in the prior art is contained in various medical textbooks, such as *Campbell's Operative Orthopedics*, and in numerous articles and patents, such as U.S. Pat. No. 6,132,468 (by the same inventor herein) and other patents and articles cited therein.

The Applicant herein, an orthopedic surgeon who specializes in repairing joints such as injured or diseased knees, has submitted a number of patents and pending patent applications which disclose several of the components of the assembled multi-component device disclosed herein. Those patents and patent applications include:

U.S. Pat. No. 6,132,468 (issued Oct. 17, 2000), which discloses (i) flexible inflatable envelopes, which can be inserted into a joint in collapsed fashion, via an arthroscopic insertion tube, and then filled with a polymer that will harden and set to form a complete implant; and, (ii) tools and templates that can be used to remove cartilage and prepare a hard bone surface, arthroscopically;

Application No. 60/192,482 and Ser. No. 09/818,811, both of which describe hydrogel components that can be reinforced by a three-dimensional woven matrix, of a type that was originally developed for entirely different materials such as used in aerospace applications;

Application No. 60/250,091, entitled "Multi-Perforated Non-Planar Device for Anchoring Cartilage Implants and High-Gradient Interfaces," which discloses a "perforated waffle" type of interfacing layer, for reinforcing and strengthening the attachment between a soft cushioning material (such as a gel) and a substantially harder surface, such as a plastic shell or bone surface.

Application Ser. No. 09/393,522, entitled "Improved Resorbable Scaffolds to Promote Cartilage Regeneration," which discloses a scaffolding structure with a rim-and-runner system comparable in various respects to the anchoring component described below.

Application Ser. No. 09/659,321, entitled "Rim Components for Use in Arthroscopic Replacement of Cartilage Using Inflatable Envelopes," which discloses flexible ring-type structures that can be inserted into a joint arthroscopically, anchored to a prepared bone surface using pins or similar devices, and then used to help position, grip, and firmly secure an envelope-type device which can also be inserted arthroscopically.

Application Ser. No. 09/690,897, entitled "Tool Set to Assist Arthroscopic Replacement of Cartilage Using Flexible Inflatable Envelopes," which discusses arthroscopic tools and tool guides that can be used to remove cartilage and prepare a hard bone surface which will be ready to receive a mass-manufactured implant.

Application Ser. No. 09/690,897, entitled "Semi-Permeable Membranes to Assist in Cartilage Repair," describes implants which are covered by semi-permeable membranes that will allow water to permeate through them readily, but which will not allow larger molecules that cause synovial fluid to be very slippery (including hyaluronic acid, lubricin, and surface-active phospholipids) to penetrate through them easily.

The teachings of the above-listed patents and patent applications are incorporated herein by reference, as though fully set forth herein. Any applications listed above which have not been issued or otherwise published by the date of issuance of any patent issuing from this current application will be laid open for public inspection and copying on that date.

In his ongoing efforts to develop improved implants for repairing or replacing cartilage, the Applicant herein has realized that a particular combination of components, arranged in a particular manner as disclosed below, can provide an improved device with a combination of highly useful traits and advantages. Such devices can be implanted entirely through arthroscopic or minimally-invasive incisions, to minimize damage and disruption to surrounding tissues and vasculature. After implantation, these devices can provide a combination of highly advantageous traits, on both the "anchoring" side (i.e., the side of an implant which presses against a supporting bone structure, such as a femoral or tibial condyle, in a knee) and the "articulating" side (i.e., the side which is exposed to synovial fluid in a joint and which will slide and rub against another cartilage or implant surface in the joint).

Accordingly, one object of this invention is to disclose an improved non-resorbable implant for repairing or replacing damaged or diseased cartilage in a joint such as a knee, wrist, ankle, or finger, and possibly in a ball-and-socket joint such as a hip or shoulder.

Another object of this invention is to disclose an improved non-resorbable implant for repairing or replacing cartilage, having both (i) a relatively pliant and non-rigid "bearing surface" which emulates the articulating surface of a segment of natural cartilage, and (ii) an anchoring portion which is sufficiently flexible to allow it to be inserted into a joint, during surgery, through an arthroscopic insertion tube.

Another object of this invention is to disclose an improved non-resorbable implant for repairing or replacing cartilage, which is thin enough to allow it to be rolled up into a cylindrical shape that can be inserted into a joint through an arthroscopic insertion tube, and then unrolled, inside the joint, in a manner which allows it to be pinned or otherwise anchored to a prepared bone surface.

Another object of this invention is to disclose an improved non-resorbable implant for repairing or replacing cartilage, made of components that are small enough to be inserted into a joint via arthroscopic methods, and then assembled in situ, inside the joint, to form a complete and functional implant.

These and other objects of the invention will become more apparent through the following summary, drawings, and description of the preferred embodiments.

SUMMARY OF THE INVENTION

A non-resorbable implant for repairing or replacing damaged or diseased cartilage in a mammalian joint (such as a knee) is disclosed. This implant uses a relatively soft and bendable "bearing surface", which is bonded or otherwise coupled (preferably through one or more intermediate layers or components that provide greater strength) to a flexible anchoring component, such as a rim or grid component, or a porous non-planar molded layer. All components which make up the implant should be flexible, so that the implant (or each component, if assembled in situ) can be rolled up and surgically inserted into a joint through a minimally invasive incision, preferably by arthroscopic means. In one embodiment, a flexible anchoring component which does not contain a bearing surface is inserted into a damaged joint through an insertion tube, opened up to its final shape inside the joint, and anchored to a prepared bone surface, using pins, cement, or other suitable means. The component with the bearing surface is then inserted into the joint, unrolled or unfolded by the surgeon, and affixed to the anchoring component. In an alternate embodiment, a unitary implant, having a gel-type bearing surface with high porosity on the articulating side, and having anchoring pegs made of the same or a compatible material but with lower porosity and greater strength on the opposed anchoring side, can be used. In either structure, the anchoring side should be made of a material which encourages ingrowth of osseous (bony, calcified) tissue, for a stronger and more permanent fixation to the supporting bone.

BRIEF DESCRIPTION OF THE DRAWINGS

FIG. 5 depicts a single-component implant as shown in FIG. 3, which has been rolled into a cylindrical arc having an angle of displacement designated as a.

DETAILED DESCRIPTION

Figure 1:
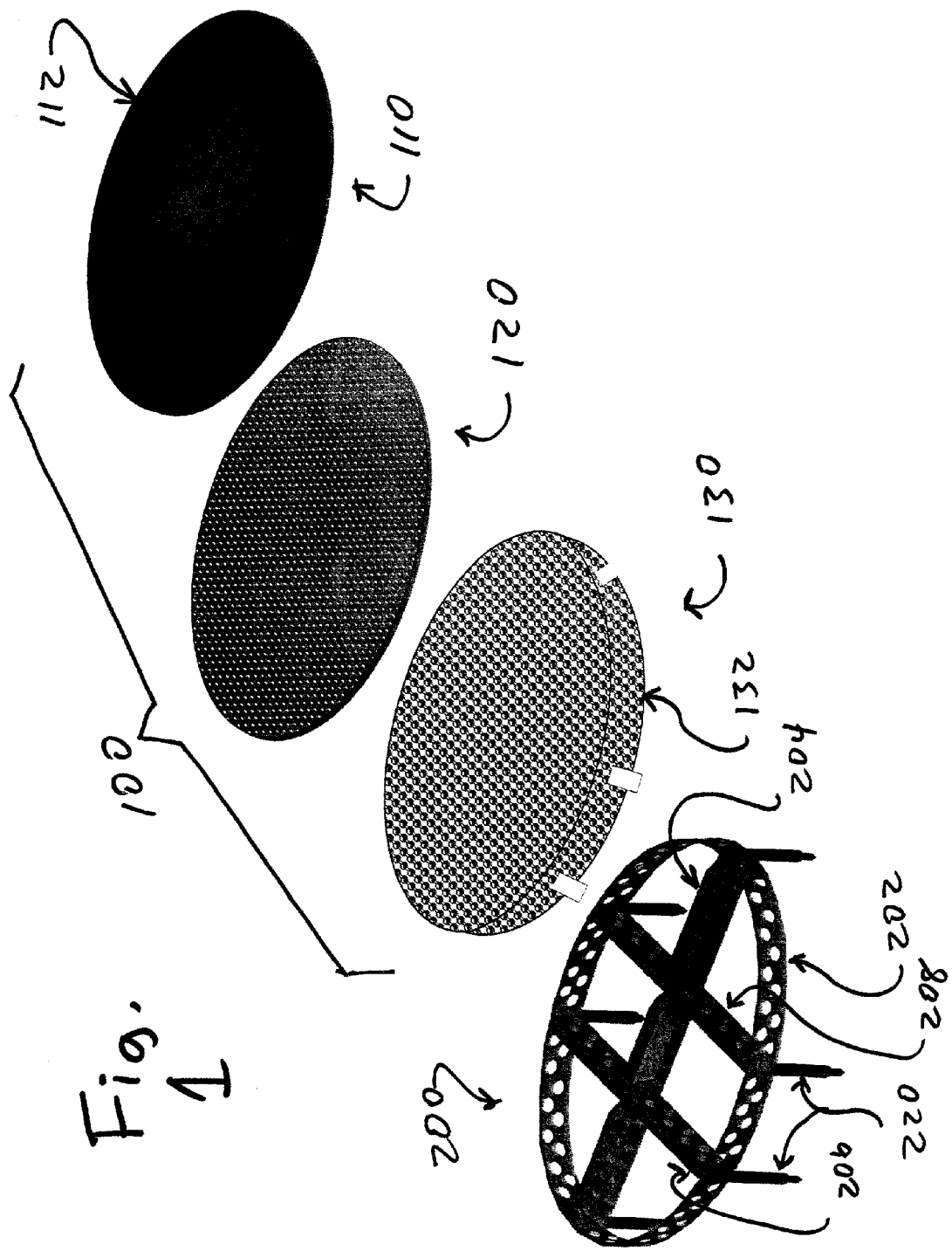
FIG. 1 depicts a flexible cartilage-replacing implant made of components that are inserted separately into a joint, and then assembled in situ (inside the joint).

To illustrate the preferred embodiments of this invention, it is assumed that an orthopedic surgeon will use a flexible implant as disclosed herein to treat a patient who is suffering from "Grade 4 chondromalacia" in a knee joint. Upon doing an arthroscopic analysis, the surgeon realizes that part of a medial femoral runner, and part of the medial tibial plateau which rubs against the femoral runner, have both become seriously abraded. On each of those two surfaces, a generally round area of cartilage has been completely worn away, exposing the underlying bone, and generating substantial pain and discomfort which caused the patient to have the knee examined. Each area of denuded bone is surrounded by roughly concentric rings of Grade 3 chondromalacia (which is less severe, with some cartilage remaining over the bone), then Grade 2 (moderate) chondromalacia, then Grade 1 (shallow surface) chondromalacia, and with generally undamaged areas of cartilage surrounding those abraded areas.

Using arthroscopic tools (including, if desired, the types of tools described in above-cited U.S. Pat. No. 6,132,468 and patent application Ser. No. 09/690,897) for cutting, gripping, scraping, and pulling, the surgeon will prepare a hard bone surface, usually in a roughly circular or elliptical area, by removing an area of cartilage from each of the affected bones (the femur, and the tibia). The exposed "spongiform" bone surfaces are then "freshened" by abrading. When those bone surfaces have been prepared, the surgeon is ready to insert two implants, one for each exposed bone surface. As used herein, any references to "hard bone surface" exclude the intramedullary canal portion of a bone, or the portion of a bone which contains the relatively soft internal portion that contains the bone marrow. Most "hard bone surface" preparations that will provide the strong anchoring attachments needed for a knee or similar joint repair will normally need to target a portion of the hard bone structure known as a "subchondral plate".

The implants disclosed herein can be manufactured in a variety of sizes and shapes. To ensure that the implant used will fit or at least closely aproximate the exposed bone surface area, the surgeon can take any of several steps, including: (i) choosing a pre-manufactured implant that is close to the final desired shape; (ii) trimming the implant as needed to ensure the best possible fit; and (iii) using a small, easily manipulated piece of material (which may be opaque and brightly colored for high visual contrast, or which may have a printed sizing grid on it) as a fitting device to help the surgeon check the exact size and shape of the prepared bone surface. By carrying out the process carefully, a skilled surgeon can modify the implant and/or the bone surface, to ensure a close-fitting accommodation between the two.

If desired, the implant can have a curved (rather than flat or planar) overall shape, to help it more closely conform to the bone surface it will be emplaced upon and the cartilage surface that is being replaced. Unless designed otherwise for a specific purpose, it is generally anticipated that each implant typically will have a thickness of several millimeters.

Each implant will have a "articulating" or "bearing" surface on one side, and an "anchoring" surface on the other side. After an implant has been installed, the anchoring surface will be pressed against the supporting bone, and the articulating or bearing surface will remain exposed to the synovial fluid which lubricates the joint. When the patient walks, the bearing surface on a femoral implant will rub and slide against the bearing surface on a tibial implant.

It is anticipated that, for most patients, both a femoral runner implant and a tibial plateau implant will be installed at the same time, in the same operation. Because cartilage is a relatively soft natural form of hydrogel, as soon as one cartilage surface in a joint becomes damaged, it becomes roughened in a way that causes it to begin abrading and damaging the cartilage surface that rubs against it. By the time grade 4 chondromalacia leads to exposed bone, both of the two cartilage surfaces that rub and slide against each other in that joint compartment will be badly damaged.

Bi-Component Implant

FIG. 1 depicts a two-component implant which will be inserted into the joint in at least two distinct pieces, which will be assembled in situ (i.e., inside the joint where it will function). An anchoring grid 200 will be securely implanted to a prepared bone surface, then a flexible implant subassembly 100 will be inserted into the joint and securely affixed to the anchoring grid 200.

The flexible implant subassembly 100 shown in FIG. 1 has three distinct layers, or zones. In a preferred embodiment, these three layers are bonded or otherwise fabricated together prior to implantation, in a controlled manufacturing operation; this can ensure proper quality control and maximum strength and stability, and it can reduce the amount of time required for the surgery if the surgeon does not have to carry out an assembly step involving these layers.

The three layers used in the implant 100 shown in FIG. 1 include a hydrogel bearing layer 110, a "perforated waffle" interface 120, and a bone ingrowth pad 130.

The hydrogel bearing layer 110 will have a very smooth articulating or bearing surface 112. It should be made of a material such as a fibrous protein and/or polymeric matrix, made of collagen fibers or any of various hydrophilic polymeric fibers that will allow water molecules to readily permeate through this layer (or at least through the uppermost portions thereof). Hydrogel materials, which can be reinforced for greater strength by a three-dimensional network of strong woven fibers if desired, are discussed in more detail in U.S. patent application No. 60/192,482 and Ser. No. 09/818, 811, cited above. In general, most hydrogel materials have porosity levels higher than about 90%, often reaching 95% or even higher. If desired, layer 110 can also be covered with an outermost semi-permeable membrane, as described in U.S. patent application Ser. No. 09/690,897.

On its opposed side, flexible implant 100 will have a bone ingrowth pad 130, with an anchoring surface 132 that will be pressed against a bone surface after implantation. In order to promote solid and stable anchoring, bone ingrowth pad preferably should promote and induce ingrowth by bony (osseous, calcified) tissue. Biocompatible materials that promote bony tissue ingrowth have been developed over the past two decades, and are known to those skilled in the art. Examples include meshes made of biocompatible metallic alloys, which can be "sputter coated", if desired, with calcium-phosphate blends that emulate hydroxyapatite, the crystalline structure that gives bones their hardness.

In a preferred embodiment, a "multi-perforated non-planar interface" component 120 (also referred to herein as a "perforated waffle" layer) can be provided between the relatively soft material of the hydrogel bearing component 110, and the substantially harder material of the bone ingrowth pad 120. This type of interface layer 120 is described in more detail in provisional application Ser. No. 60/250,091, cited above and incorporated by reference herein. A small segment from such a layer, shown in a perspective cutaway view, is provided in FIG. 2. This cutaway drawing depicts two of the numerous "riser bumps" 40 that will be arrayed in a geometric pattern in interface layer 120. Suitable geometric patterns can include rectangular, diamond, or hexagonal arrays, or any other suitable pattern.

Each riser bump 40 in layer 120 has one or more semi-vertical sides or facets 42 (rising out of the "baseline" or "grid" layer 32), as well as a relatively horizontal upper surface 44 (all references herein to directions such as vertical or horizontal assume that the grid 30 is horizontal). The semi-vertical sides 42 preferably should be provided with rounded corners, if any corners are present, to minimize any risk of internal cutting, abrasion, or similar damage (such as, for example, if a patient with one of these implants in a knee or hip falls or must jump from an elevated height, and the knee or hip undergoes an instant of high compression during impact). For similar reasons, any riser bump 40 should have a flat horizontal upper surface 44, to minimize any risk that a sharp or spiked surface might be pushed into or through the soft material which will overlay it.

Figure 2:
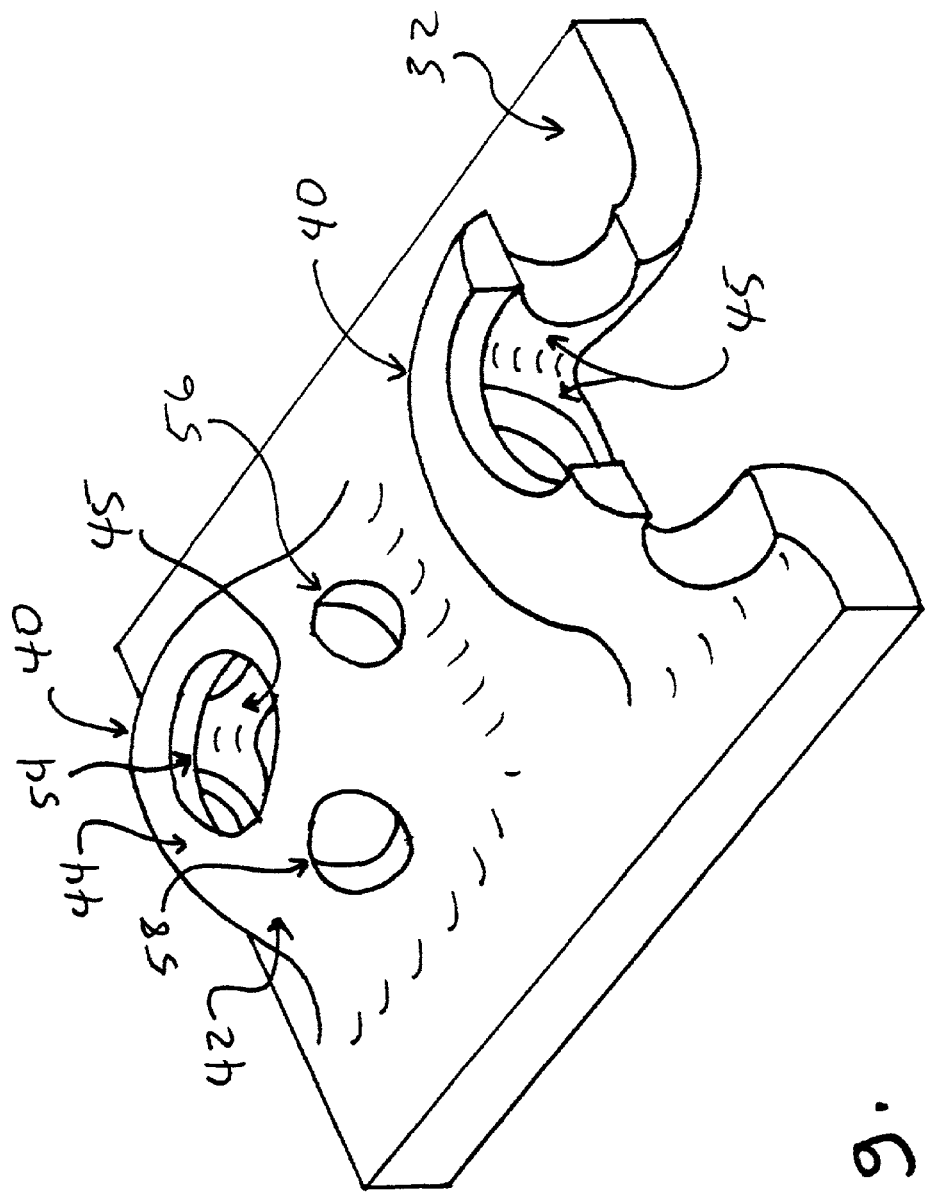
FIG. 2 is a cutaway perspective view of a small segment of a "perforated waffle" layer which can be used to provide a stronger interface between a soft hydrogel layer, and a much stiffer and harder anchoring layer.

As shown in FIG. 2, each roughly vertical facet 42, and horizontal facet 44, has a hole (which can also be called a perforation, orifice, aperture, etc.) passing through it, shown in FIG. 2 as horizontal holes 54, longitudinal holes 56, and transverse holes 58.

Acting together, riser bumps 40 and the numerous perforations 54-58 which pass through the riser bumps in various directions create a complex non-planar multi-perforated outer surface, in interface layer 120. In addition, as can be seen from the visible "inner walls" or "underside walls" 45, shown in FIG. 2, the outer-surface facets 42 and 44 are further supplemented by still more surfaces or facets, on the underside of the interface layer 120. All of those surfaces or facets are exposed and accessible to the water molecules in a gel compound. Therefore, all of those surfaces or facets can resist fluid pressure which is imposed on those facets. In this manner, the complex surface geometry of interface layer 120 can allow this layer to use fluid flow, within a hydrogel, to redistribute and disseminate, in a more balanced, even, and reinforced manner, the compressive and/or shear forces that are imposed on the articulating surface 112 of the flexible implant subassembly 100.

The interface layer 120 can be bonded, fused, or otherwise secured to the bone ingrowth pad 130, using any suitable method (such as a chemical adhesive, using targeted heat to soften and melt the appropriate surfaces of two polymeric layers so they will fuse together, using a welding step if the two layers are made of metal, etc.). Alternately, it may be possible to fabricate both layers from a single type of material, such as by a combination of techniques that might include, for example: (i) molding a polymeric compound in a mold which is partially occupied, in the bottom layer, by a granular compound (such as salt, sugar, etc.) that can subsequently be dissolved by water or a suitable solvent; (ii) dissolving and removing the granules, thereby creating a porous structure on the bottom layer which promotes cell ingrowth; and, (iii) machining the top layer by means of laser beams, small drill bits, or other suitable means, to create the multiple non-planar perforations on the riser bumps.

The implant subassembly 100, when fully fabricated, should be sufficiently flexible to allow it to be rolled up into a cylinder, and loaded into an arthroscopic insertion tube. It will be inserted into a joint which has already been prepared, by placement of an anchoring grid 200, as shown in FIG. 1.

Anchoring Grid

FIG. 1 illustrates one potential design for an anchoring grid 200, which has a rim 202, a longitudinal runner 204, two transverse runners 206 and 208, and anchoring pins 220.

Anchoring pins 220 are illustrated in FIG. 1, to indicate their placement. In one preferred embodiment, anchoring pins 220 will be not be manufactured as an integral part of anchoring grid 200, since they are likely to interfere with an arthroscopic insertion process if they are fixedly attached to the grid 200. Accordingly, they can be inserted into the joint by the surgeon after the grid 200 is already in place, and driven through accommodating eyelets or similar holes positioned around the periphery of the grid 200.

In an alternate preferred embodiment, it may be possible to manufacture pins 220 as part of the anchoring grid 200, by attaching them to remainder of the grid 200 by means of hinges, flaps, or other means that will allow the pins to be rolled up into a tubular form, to allow grid 200 to ne squeezed into (and through) an arthroscopic insertion tube. In addition, as noted above, the entire implant as disclosed herein can be adapted for use in "open joint" surgery; if prepared for use in that embodiment, the pins can be firmly and rigidly attached to the anchoring layer.

In the embodiment shown in FIG. 1, anchoring grid 200 is shown with "walls" comprising a peripheral rim 202 and runners 204-208. For purposes of this disclosure, it is believed that this type of layout may be able to provide several potentially important advantages, because of the way the various wall components, and the internal compartments created by the rim and runners, can interact with bone ingrowth pad 130.

As one example of a potential advantage of this layout, the reinforced and relatively strong rim 202 can provide provide any of several potentially useful options for securely attaching the flexible implant 100 to the anchoring grid 200, without having to use one or more anchoring pins or similar devices that would need to penetrate the center portion of the bearing surface 112. In addition, the runners 204-208 inside rim 202 can help ensure that the rim 202 will return to the proper shape, after being rolled up and forced through an arthroscopic insertion tube. Third, it may be possible to use a strong cement (such as a poly-methyl-methacrylate (PMMA), or a polycarbonate and/or urethane mixture) to chemically bond an anchoring grid 200 to a bone, in a manner which will prevent the cement from clogging and interfering with the desired porosity of the underside of bone ingrowth pad 130. And fourth, the layout of the anchoring grid 200 can help ensure that during initial recuperation after surgery, before substantial bone ingrowth into the bone ingrowth pad 20 has occurred, the bone ingrowth pad 20 will remain immobilized and stationary, and will not slide or shift on the bone surface that was prepared at the start of the surgery.

These factors (and other lesser factors) suggest to the Inventor herein that an embodiment of the implant disclosed herein, which will be preferred for at least some patients, is likely to use an anchoring grid that will include: (i) a rim, which will interact with anchoring pins that will be driven directly into hard bone material; (ii) one or more internal runners, which will divide the anchoring grid into internal compartments, in an arrangement such as (but not necessarily identical to) the arrangement shown in FIG. 1. That type of grid may be able to interact with a bone ingrowth pad, in ways that would be difficult to provide using a bone ingrowth pad alone (or bonded to other covering layers).

It should be noted that in the embodiment shown in FIG. 1, the walls which make up rim 202 and runners 204-208 of the anchoring grid 200 are provided with a plurality of orifices (also called apertures, openings, holes, etc.). Such orifices (which may be filled with permeable material that promotes bone tissue ingrowth) can be used if animal tests indicate that they promote better anchoring of the implant to the surrounding tissue. Such anchoring may be generated by scar tissue, by bony tissue ingrowth, or some combination thereof, depending on the cutting and sculpting steps used in a particular patient, which will determine the size, shape, and positioning of the contact area between the implant and the surrounding tissue.

It should also be noted that an anchoring grid of this nature may provide the option of periodically replacing the bearing pad of an implant, in a manner which is relatively simple and non-traumatic for the patient.

Unitary Implant

Figure 3:
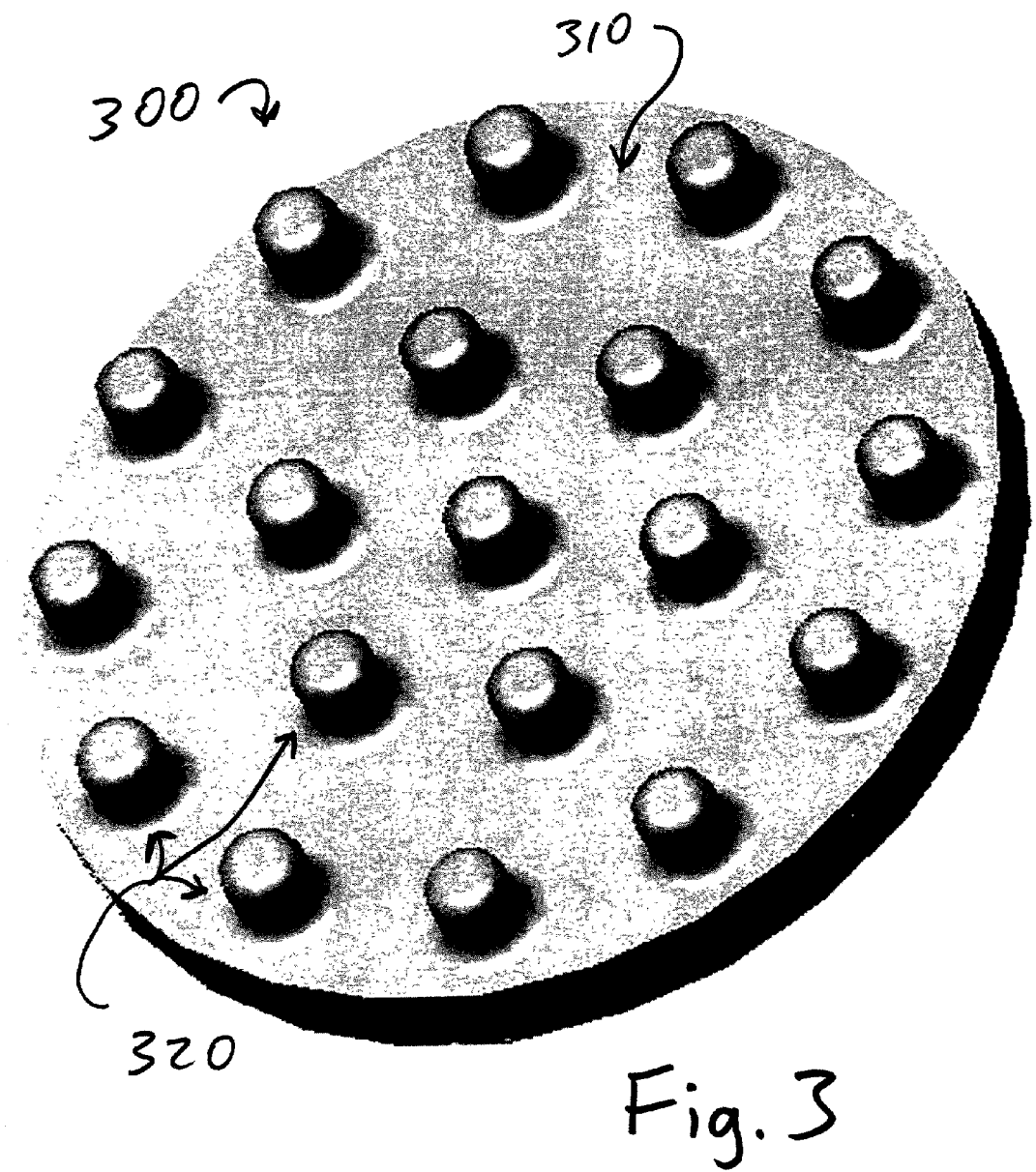
FIG. 3 depicts a unitary implant, made of a hydrophilic fibrous matrix which has a density/porosity gradient that allows the smooth articulating surface to be a high-porosity hydrogel, while the anchoring pegs have much less porosity and are much stiffer and stronger.

In contrast to the two-component system described above, in which an anchoring grid 200 is inserted into a joint and firmly anchored to a bone before the remainder of the implant 100 is inserted and affixed to the anchoring grid, FIG. 3 depicts the anchoring surface 310 of a "unitary" implant 300 that can be fabricated as a single unit, in a manufacturing facility, and then rolled up for insertion into a joint through an arthroscopic insertion tube.

The anchoring surface 310 of implant 300 contains an array of protrusions or "pegs" 320, having a uniform size and a symmetric geometric pattern, so that they can fit in a fairly snug and secure manner into accommodating holes, which can be drilled into a prepared bone surface with the aid of a template that will cause the holes to match the pattern of the pegs 320.

It is anticipated that a common size for unitary implant 300 will typically be in a range of about 1 to about 3 centimeters in diameter, and that anchoring pegs 320 will be typically be within a range of about 3 to about 7 mm in diameter.

The unitary implant 300 can be manufactured as a single item, by creating a fairly steep density/porosity gradient between the hydrogel bearing surface 330, and the anchoring pegs 320. The relatively soft and open hydrogel on the bearing surface 330 will have very high porosity, anticipated to be in the range of at least 80% pore space (with less than 20% of its volume taken up by the fibrous matrix). By contrast, the much stiffer and harder anchoring pegs 320 will have much lower porosity, anticipated to be in the range of about 20% or less pore space, with 80% of its volume made of fibers. This type of gradient can be created by various known means, which include: (i) using centrifugation, filter pressing, or other compaction or pressurizing techniques to compress fibers into the molding vacancies that will create the anchoring pegs; (ii) sequential crosslinking and/or compaction steps (triggered or controlled by chemicals, radiation, etc.) with additional fibrous material added between different crosslinking steps; or, any other conventional or hereafter-discovered method which is suitable for creating the types of density and compaction gradients that are anticipated herein.

Flexibility

Figure 4:
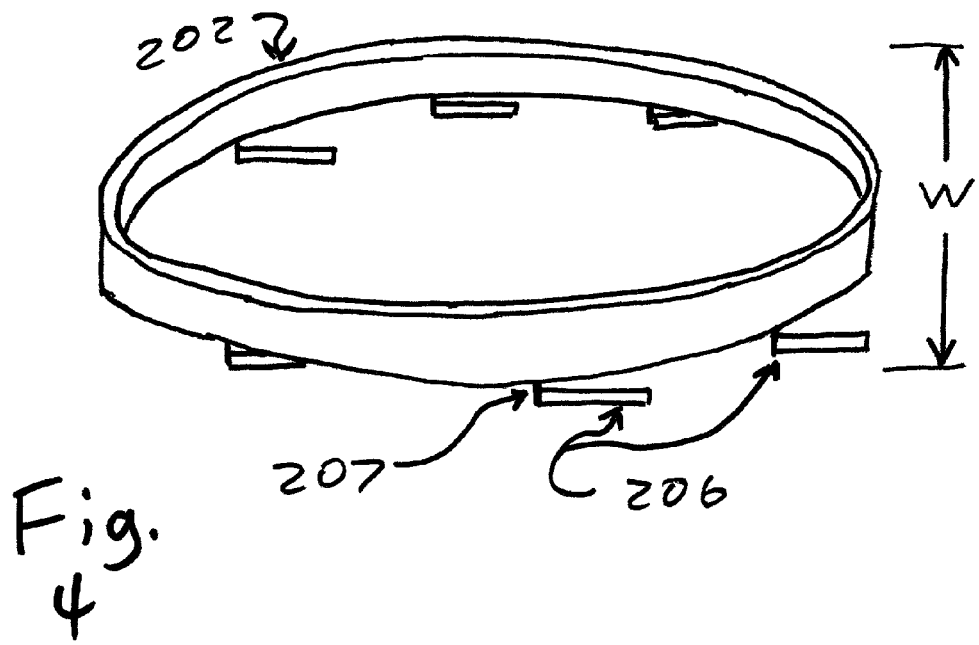
FIG. 4 depicts a flexible rim of a bi-component anchoring grid, which has been squeezed to give it a smaller width, and which has had its anchoring pins rotated to a trailing/inserting position by means of hinges or flexible flaps which attach the pins to the rim.

As used herein, a "flexible" anchoring rim, in a bicomponent systems as shown in FIG. 1, indicates that the rim can be squeezed until its width is about 75% or less of its relaxed width, as shown in FIG. 4. FIG. 4 also indicates that anchoring pins 206 have been folded into a relatively flat "trailing" or "inserting" position, by means of hinges or flaps 207 which couple the pins 206 to the rim 202.

Figure 5:
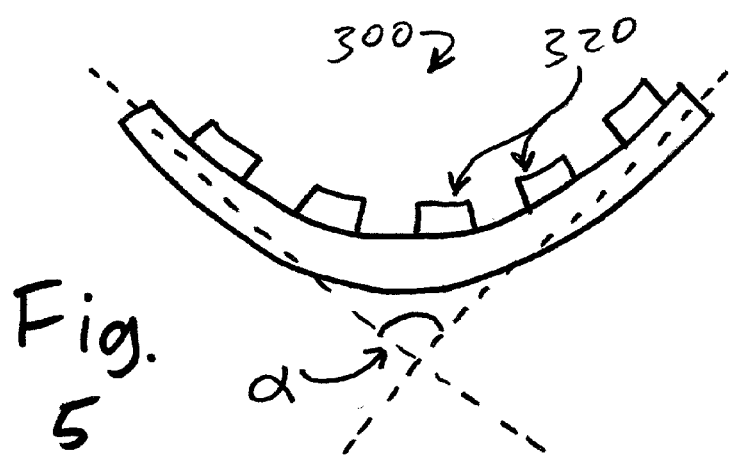

As used herein, a "flexible" unitary implant 300 can be rolled into a cylindrical arc which has an "angle of displacement" (designated as a in FIG. 5) that is about 110 degrees or less. It is anticipated that the unitary implants disclosed herein will be capable of being rolled into a complete tube.

These (or greater) degrees of flexibility can help minimize tissue disruption as an implant is being inserted into a joint.

Additional Comments

To be useful as disclosed herein, a cartilage repair implant must be flexible, in a manner that allows it to be inserted into a joint that is being surgically operated on, through a minimally invasive incision (preferably using arthroscopic devices and methods). This does not mean, however, that the implant must be flexible in the same manner, in all directions. Instead, as one example, an anchoring layer can be made of relatively stiff material (such as metallic strands, or relatively thick and stiff polymeric strands) in one direction (such as the "longitudinal" direction, which is the longest axis of the implant). A different and more flexible material (such as nylon strands, or substantially thinner polymeric strands) can be used in the "transverse" direction, to hold the thicker and stiffer longitudinal strands together. This approach can allow an anchoring layer to be curled up fairly tightly in one direction, but not in the other. That type of one-directional or "selective" flexibility can be highly useful for allowing arthroscopic insertion of a rolled-up implant into a joint.

Various other approaches can also (or alternately) be used, to provide a desired and/or manipulable type or degree of flexibility during the implant insertion procedure. As one example, an anchoring mesh made of a "semi-cured" polymer or similar material which is relatively soft and flexible can be used to provide the anchoring component. In its soft and flexible pre-surgical form, it can be rolled up into a relatively tight cylinder or spiral. After it has been inserted into a joint, unrolled, and tacked down to a bone, it can be subjected to a treatment (such as ultraviolet radiation, through fiber optic cables that terminate in a flattened spatula, with an opaque shield on one side to protect tissue from the UV radiation) that will cause it to become substantially stiffer and harder.

In some respects, the methods that will be used to insert and anchor a flexible implant as disclosed herein may be analogous to unrolling a segment of carpet (which has different layers of backing and tufting) across a floor.

Briefly, the flexible implant (which, in most cases, presumably will not be more than a few millimeters thick) will be rolled up into a cylindrical shape, which must be thin enough to be pushed through a minimally invasive incision, using an insertion tube, into a joint that has been prepared to receive the implant. In one embodiment, as it is pushed out of the end of the tube, it will spontaneously unroll, seeking to regain its manufactured shape. As or after it unrolls, it can be positioned, tacked down as needed, and permanently anchored.

In an alternate embodiment, the material can be wrapped around a center core, in a manner which allows it to be unwrapped as it is moved across a bone surface, under the control of the surgeon. As it is unrolled, it is "tacked down" around its periphery by sutures, small pins, or other comparable devices, which can be driven down into the relatively spongy outer bone layer in a controlled manner that prevents them from subsequently causing cutting or abrasion. Such sutures or pins can be connected to the implant by suitable means, such as small eyelets or loops that extend downward from bone ingrowth pad 130 or from any woven fibrous material that is embedded in a soft outer layer 110.

Regardless of which method of unrolling is used, after an implant has been fully unrolled, positioned, and tacked down, it can be permanently anchored to the bone.

It should be noted that the anchoring layer does not need to be highly flexible, to a point of allowing the device to be rolled up into a tight spiral. So long as sufficient flexibility is provided in the anchoring layer to allow the implant to be flexed into a shape that is not as wide as the implant will be after it is fully anchored (for example, if two opposed sides or ends of the device can be curled toward each other, to form a simple U-shaped or similar configuration), then that degree of flexibility will allow the implant to be inserted through a "minimally invasive" incision, as that term is interpreted and applied. In determining the value of this type of implant in surgery on a damaged joint, the question is not whether a flexible device will fit through a standard, conventional arthroscopic insertion tube. Instead, the pertinent question is whether this new type of flexible implant can be inserted through a smaller incision (which will cause less tissue and blood vessel damage and disruption, thereby allowing faster recovery with less pain and scarring) than would be required for a non-flexible implant of the same size.

Thus, there has been shown and described a new and useful means for creating improved implants for repairing cartilage in joints such as knees. Although this invention has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

The invention claimed is:

1. A flexible surgical implant for repairing damaged hyaline cartilage in an articulating mammalian synovial joint, comprising:
    an anchoring portion having a plurality of anchoring protrusions and an anchoring surface structured to support tissue ingrowth, the anchoring portion forming a first side of the implant configured for fixation to one bone surface of the joint;
    a bearing surface portion forming an opposite side of the implant, the bearing surface portion comprising a hydrogel material providing an exposed lubricious surface configured to rub and slide over an opposing surface of the joint;
    wherein the implant is sufficiently thin and flexible to be deformed from an original manufactured shape into a form having a width of about 75% or less than that of the original manufactured shape, for arthroscopic insertion into the joint, and resumes the original manufactured shape when released in the joint.

2. The flexible surgical implant of claim 1, wherein the implant comprises an assembly of the anchoring portion and the bearing surface portion.

3. The flexible surgical implant of claim 1, wherein the anchoring portion and the bearing surface portion are separate components and the anchoring portion comprises a rim with a shape memory holding the original manufactured shape, the rim being sufficiently flexible to be squeezed for said arthroscopic insertion and brings the implant back into the original manufactured shape when released.

4. A flexible surgical implant for repairing damaged hyaline cartilage in a mammalian synovial joint having two articulating bones, comprising:
    an anchoring portion having a plurality of anchoring protrusions and an anchoring surface structured to support tissue ingrowth, the anchoring portion forming a first side of the implant adapted for fixation to one of the bones;
    a bearing surface portion forming an opposite side of the implant, the bearing surface portion comprising a hydrogel material providing an exposed lubricious hydrogel surface configured for slidable articulating on a surface of the other of the bones;
    wherein the implant is sufficiently thin and flexible to be rolled from an original manufactured shape into a cylindrical arc for arthroscopic insertion into the joint wherein the opposed edges of the arc have an angular displacement of 110 degrees or less, and to resume the original manufactured shape when released in the joint.

5. A surgical implant for repairing damaged hyaline cartilage in a mammalian synovial joint with two articulating bones, comprising:
    an anchoring layer defining a surface one side of the implant, the anchoring layer having at least one of raised bumps, openings and pins configured for fixing the implant to one of the articulating bones,
    a bearing surface layer on an opposite side of the implant, said bearing surface layer comprising a flexible hydrophilic polymer with a smooth and lubricious articulating surface exposed to a surface of the other of the articulating bones,
    wherein the surgical implant seeks an original manufactured shape and is sufficiently flexible to be compressed to fit through a minimally-invasive incision by arthroscopic means, and assumes the original manufactured shape when released inside the joint.

6. The flexible surgical implant of claim 5, wherein the bearing surface layer comprises a hydrogel.

7. The flexible surgical implant of claim 5, further comprising a plurality of anchoring components that extend below the surface defined by the anchoring layer.

* * * * *